(12) United States Patent
Atwell

(10) Patent No.: US 12,256,972 B2
(45) Date of Patent: Mar. 25, 2025

(54) MONOPOLAR PLASMA COAGULATION RADIAL ANTENNA TIP DESIGN

(71) Applicant: GYRUS MEDICAL LIMITED, Cardiff (GB)

(72) Inventor: Anthony Atwell, Newport (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 635 days.

(21) Appl. No.: 17/172,251

(22) Filed: Feb. 10, 2021

(65) Prior Publication Data
US 2021/0259756 A1  Aug. 26, 2021

(30) Foreign Application Priority Data

Feb. 25, 2020 (GB) ..................................... 2002656

(51) Int. Cl.
| | |
|---|---|
| *A61B 18/14* | (2006.01) |
| *A61B 18/04* | (2006.01) |
| *A61B 18/12* | (2006.01) |
| A61B 18/00 | (2006.01) |

(52) U.S. Cl.
CPC ........ *A61B 18/042* (2013.01); *A61B 18/1206* (2013.01); *A61B 18/14* (2013.01); *A61B 2018/00583* (2013.01); *A61B 2018/00589* (2013.01); *A61B 2018/1253* (2013.01)

(58) Field of Classification Search
CPC ............ A61B 18/042; A61B 2018/048; A61B 2018/00583; A61B 2018/1253
See application file for complete search history.

(56) References Cited

U.S. PATENT DOCUMENTS

| | | | | |
|---|---|---|---|---|
| 5,720,745 A | * | 2/1998 | Farin .................... | A61B 18/042 606/49 |
| 6,958,063 B1 | * | 10/2005 | Soll ...................... | A61B 18/042 606/49 |

(Continued)

FOREIGN PATENT DOCUMENTS

| | | |
|---|---|---|
| GB | 2508956 A | 6/2014 |
| GB | 2573128 A | 10/2019 |

OTHER PUBLICATIONS

Jul. 22, 2020 Search Report issued in GB Patent Application No. GB2002656.3.

*Primary Examiner* — Sean W Collins
(74) *Attorney, Agent, or Firm* — Oliff PLC

(57) ABSTRACT

A monopolar ionisable gas plasma coagulation applicator includes: an elongate shaft extending from a proximal end to a distal end, and defining a hollow inner volume and a longitudinal axis of the applicator; an applicator tip mounted on the distal end of the elongate shaft, wherein the applicator tip defines an aperture extending parallel to the longitudinal axis; and an electrode extending through the inner volume and with the applicator tip, the electrode includes an open channel having an electrode tip, wherein the electrode tip is received within the hollow inner volume of the shaft and the aperture of the applicator tip to define a gas flow channel defined by the electrode and the elongate shaft and by the electrode and the applicator tip, the gas flow channel extending parallel to the longitudinal axis within the elongate shaft and extending outwards along the longitudinal axis within the applicator tip.

10 Claims, 1 Drawing Sheet

(56) References Cited

U.S. PATENT DOCUMENTS

| | | | |
|---|---|---|---|
| 2005/0118350 A1* | 6/2005 | Koulik | H05H 1/44 219/121.36 |
| 2013/0090644 A1* | 4/2013 | Williams | A61B 18/042 606/49 |
| 2013/0274742 A1* | 10/2013 | Schnitzler | A61B 18/042 606/49 |

* cited by examiner

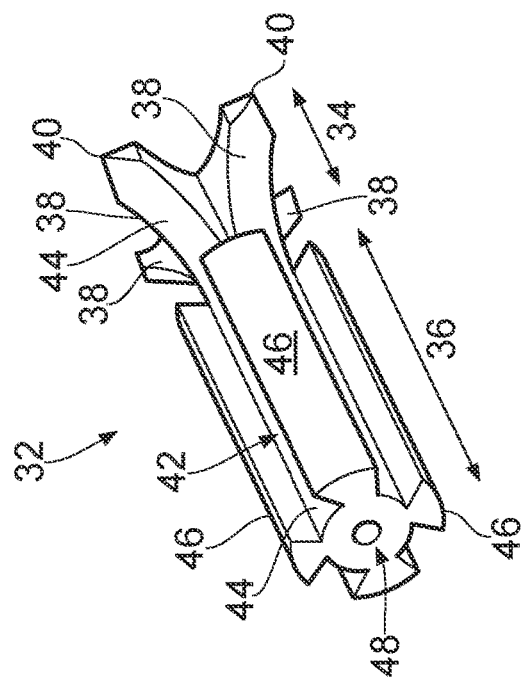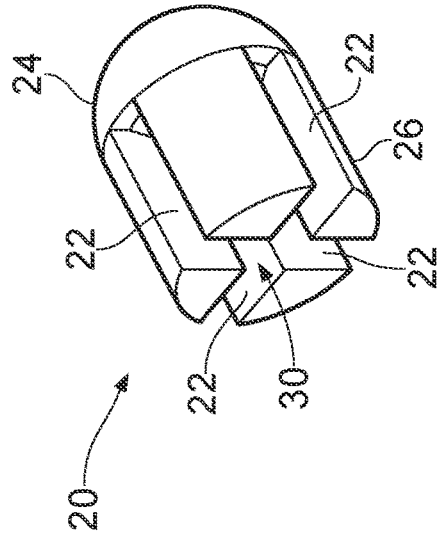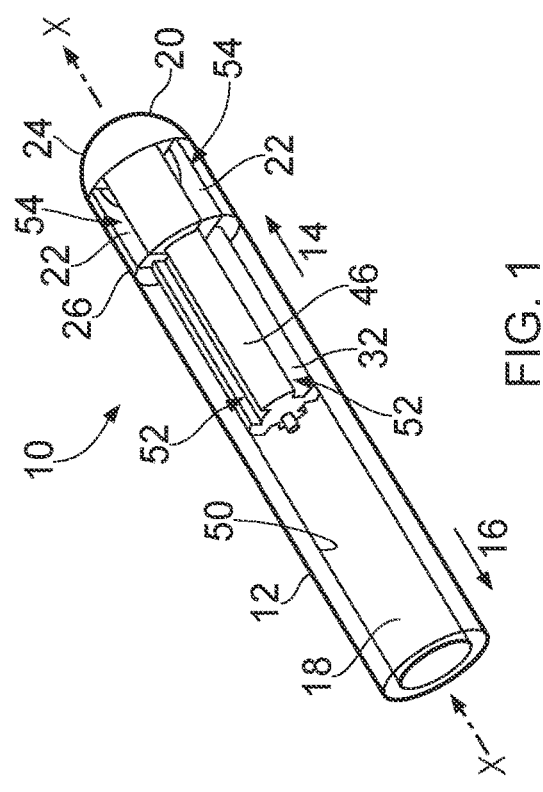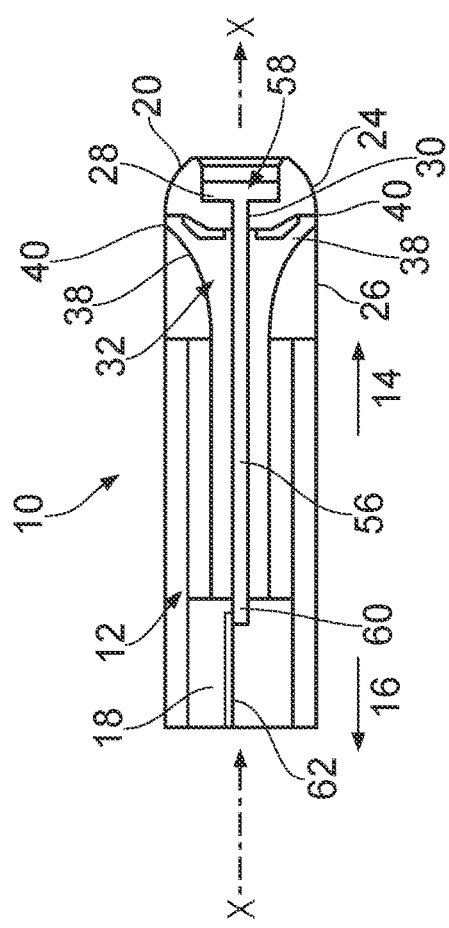

MONOPOLAR PLASMA COAGULATION RADIAL ANTENNA TIP DESIGN

The present invention relates to a monopolar plasma coagulation applicator, such as, but not limited to a monopolar argon plasma coagulation (MAPC) applicator, and similar applicators using alternative gases that can be ionised, such as helium and/or carbon dioxide. In particular, the present invention relates to such applicators having one or more radial gas flow channels.

BACKGROUND OF THE INVENTION

Argon Plasma Coagulation (APC) is an example of a non-contact monopolar electrocoagulation technique, initially used for endoscopic surgical procedures in the digestive tract. APC is typically used for superficial haemostasis and tissue ablation.

The applicator probe contains an electrode through which a high frequency electrical current is delivered to the target tissue using ionised argon gas (argon plasma). This results in coagulation of the target tissue.

The depth of coagulation is dependent on the power of the electrosurgical generator, the distance between the probe and the target tissue, and the duration of application.

However, conventional MPAC probes exhibit poor performance with respect to plasma ignition and sustain distance, particularly when the probe tip is wet. The effect of poor wet ignition and sustain performance results in the non-contact MAPC probe being used more like a contact coagulation probe.

This poor performance relates to disturbed argon flow. A single electrode in the centre of the conventional MAPC antennas is often poorly centralised and can restrict the argon flow to one of the multiple openings at the antenna tip.

A further problem often observed is the poor retention of the ceramic tip on the antenna body, resulting in frequent detachment during clinical use.

There is therefore a need for an improved applicator probe design which addresses the problems of the prior art electrocoagulation techniques using gases that can be ionised, such as argon gas, helium gas and carbon dioxide gas.

SUMMARY OF THE INVENTION

A first aspect of the present invention provides a plasma coagulation applicator comprising: an elongate shaft extending from a proximal end to a distal end thereof, and defining therein a hollow inner volume and a longitudinal axis of the applicator; an applicator tip mounted on the distal end of the elongate shaft, wherein the applicator tip defines an aperture extending parallel to the longitudinal axis; and an electrode extending through the inner volume and in contact with the applicator tip, the electrode comprising an open channel having an electrode tip, wherein the electrode tip is received within the hollow inner volume of the shaft and within the aperture of the applicator tip to define a gas flow channel defined by the electrode and the elongate shaft and by the electrode and the applicator tip, the gas flow channel extending parallel to the longitudinal axis within the elongate shaft and extending radially outwards with respect to the longitudinal axis within the applicator tip.

In one embodiment, the applicator tip comprises a plurality of apertures extending parallel to the longitudinal axis and the electrode comprises a plurality of open channels, each open channel having a respective electrode tip, wherein each electrode tip is received within a respective aperture of the applicator tip to define a gas flow channel and wherein each gas flow channel extends parallel to the longitudinal axis within the elongate shaft and extends radially outwards with respect to the longitudinal axis within the applicator tip.

It is to be appreciated that the number of flow channels can be varied from one up to the maximum that can be physically accommodated within the outside diameter of the applicator.

Where there is a plurality of electrode tips, the electrode tips are electrically common.

Preferably, the electrode is centrally located within the inner volume. This allows symmetry to be applied and each of the plurality of gas flow channels to be the same size as one another.

In one embodiment, the portion of each open channel of the electrode within the applicator tip defines a smooth curve. The smooth curve of the or each channel provides the advantage of avoiding disturbing the gas flow.

In a further embodiment, each of the plurality of electrode tips are located at an outer surface of the applicator tip. This reduces the distance between the between the electrode and the tissue, thus maximising plasma ignition and sustaining the distance between the applicator tip and adjacent tissue being treated.

In one embodiment, the distal end of the applicator tip is provided with a counter bore.

A headed pin may be received within the counter bore and extend through the applicator tip and electrode in a proximal direction along the longitudinal axis. The headed pin serves to prevent the applicator tip from detaching from rest of the applicator during use. The counter-bore in the applicator tip ensures that there is no direct tissue contact with the head of the retaining pin, which is at electrode potential during use. Alternatively, any other suitable means of retaining the applicator tip in secure engagement with the rest of the applicator may be used in addition to or instead of using the headed pin.

The proximal end of the headed pin is retained within the shaft by engagement with the proximal end of the electrode.

The applicator tip may comprise a moulded ceramic. However, it is to be appreciated that the applicator tip may comprise any other suitable non-electrically conductive material known to the skilled person and suitable for function. Further, it is to be appreciated that the applicator tip may be 3D printed or formed by grinding as an alternative to be being moulded.

Preferably, the applicator is further provided with an electrical conduit in electrical engagement with the electrode. Preferably, the electrical conduit comprises a wire carrying current to the electrode.

Preferably, the proximal end of the headed pin and/or the electrical conduit are welded to the proximal end of the electrode.

The gas flow channel may receive argon during use. However, it is to be appreciated that the gas flow channel may receive helium gas or carbon dioxide gas in addition to or as an alternative to argon gas.

BRIEF DESCRIPTION OF THE DRAWINGS

FIG. 1 is a perspective view of a first embodiment of an applicator in accordance with the present invention showing the elongate shaft in cross-section and the applicator tip in full;

FIG. 2 is a cross-sectional view of the applicator of FIG. 1;

FIG. 3 is a perspective view of the electrode of the applicator of FIG. 1; and

FIG. 4 is a perspective view of the applicator tip of the applicator of FIG. 1.

DETAILED DESCRIPTION OF THE PREFERRED EMBODIMENTS

The present invention is described with reference to FIGS. 1 to 4 in which common reference numerals are used to indicated corresponding features in different figures. The embodiment described relates to a monopolar argon plasma coagulation (MAPC) applicator. However, it is to be appreciated that any ionisable gas could be used as an alternative to argon.

FIGS. 1 and 2 show views of an embodiment of an applicator 10, and more specifically a MAPC applicator, in accordance with the present invention. Applicator 10 comprises an elongate shaft 12 extending from a distal end 14 to a proximal end 16, and defines therein a hollow inner volume 18. Elongate shaft 12 defines a longitudinal axis X of applicator 10.

Applicator 10 is further provided with an applicator tip 20 mounted on the distal end 14 of elongate shaft 12. In the embodiment shown in the figures, applicator tip 20 preferably comprises ceramic. However, it is to be appreciated that any other suitable non-electrically conducing material suitable for function could be used instead.

Applicator tip 20 has a distal portion 24 and a proximal portion 26. The distal portion 24 of applicator tip 20 is provided with a centrally located counter-bore 28 and corresponding aperture 30 extending from counter-bore 28 through distal portion 24 of applicator 10. Aperture 30 further extends through the proximal portion 26 of applicator tip 20.

Proximal portion 26 of applicator tip 20 further defines a plurality of apertures extending parallel to longitudinal axis X and equally spaced around elongate shaft 12. Each aperture is open to the exterior of applicator 10, forming an open channel 22 along the proximal portion 26 of applicator tip 20. Proximal portion 26 of applicator tip 20 butts against distal end 14 of elongate shaft 12.

Electrode 32 comprises a distal portion 34 and a proximal portion 36. As shown in FIG. 3, distal portion 34 of electrode 32 comprises a plurality of identical electrode tips 38 extending from proximal portion 36 of electrode 32. However, it is to be appreciated that electrode 32 may comprise any suitable number of electrode tips 38, the number being only limited by space available within the applicator 10. Each electrode tip 38 comprises a narrowed tip portion 40. The electrode 32 in the described embodiment comprises stainless steel.

However, any other suitable electrically conducting material suitable for purpose may be used as an alternative to stainless steel.

Proximal portion 36 of electrode 32 comprises a plurality of open channels 42, each channel defining an argon flow channel having a flow surface 44. Each flow surface 44 extends through the proximal portion 36 and into the distal portion 34 of electrode 32 to form an electrode tip 38. Each flow surface 44 is separated from adjacent flow surfaces 44 by body portion 46. Aperture 48 is provided extending through both the distal portion 34 and proximal portion 36 of electrode 32, aperture 48 extending along longitudinal axis X.

Proximal portion 36 of electrode 32 is located within elongate shaft 12 such that body portions 46 are adjacent the inner surface 50 of elongate shaft 12, thereby defining closed argon flow channels 52 between inner surface 50 of elongate shaft 12 and open channels 42 of electrode 32.

Distal portion 34 of electrode 32 is received within proximal portion 26 of applicator tip 20. Each electrode tip 38 is received within a respective open channel 22 in proximal portion 26 of applicator tip 20, such that the narrowed tip portion 40 of each electrode tip 38 is presented at the surface of the applicator 10 at the most distal part of respective open channel 22 in applicator tip 20. By locating the narrowed tip portions 40 at the surface of applicator 10, distance between the electrode 32 and the tissue being treated is reduced, thus maximising the plasma ignition and sustain distances between the applicator 10 and the tissue being treated.

Distal portion 34 of electrode 32 and each respective open channel 22 of applicator tip 20 together form a plurality of identical open argon channels 54 in the proximal portion of applicator tip 20. Each open argon channel 54 extends from respective flow surface 44 from the proximal portion 36 of electrode 32 through the distal portion of electrode 32 to guide argon gas through the applicator 10 and out of the applicator tip 20 at regularly spaced intervals around proximal portion 26 of applicator tip 20.

Although the embodiment described has a plurality of identical open argon channels 54 in the proximal portion of applicator tip 20, it is to be appreciated that the open argon channels 54 may be of similar or different cross-sectional shapes. For example, depending on the physical space available to accommodate the channels, channels of non-identical shapes may be preferable.

The identical open argon channels 54 in applicator tip 20 extend radially from applicator 10 and each open argon channel 54 comprises a smooth curve. This avoids disturbing the argon flow.

A ceramic retaining pin 56 extends through aperture 30 of applicator tip 20 and aperture 48 of electrode 32 such that the head 58 of retaining pin 56 is located within counter-bore 28 in distal portion 24 of applicator tip 20. The counter-bore in the ceramic applicator tip 20 ensures that there is no direct tissue contact with the head 58 of retaining pin 56 which, in use, would be at electrode potential.

The proximal end 60 of retaining pin 56 is secured to the proximal end of electrode 32. The proximal end 60 of retaining pin 56 is preferably welded to the proximal end of electrode 32. However, if appropriate, a suitable adhesive could be used as an alternative.

Wire 62 is also electrically secured, preferably welded, to the proximal end of electrode 32. Alternatively, wire 62 may be electrically secured to the proximal end of electrode 32 by crimping. Wire 62 provides electrical current to applicator 10.

In use, an argon supply would provide argon gas to applicator 10. Argon gas would flow through closed argon channels 52 and into open argon channels 54 before exiting applicator 10 at narrowed tip portions 40 of electrode tips 38, for plasma ignition and tissue coagulation in the normal manner at the tissue being treated.

The invention claimed is:

1. A monopolar plasma coagulation applicator comprising:
    an elongate shaft extending from a proximal end to a distal end thereof, and defining therein a hollow inner volume and a longitudinal axis of the applicator;

an applicator tip mounted on the distal end of the elongate shaft, wherein the applicator tip comprises a plurality of apertures extending parallel to the longitudinal axis; and an electrode extending through the inner volume and in contact with the applicator tip, the electrode comprising a plurality of open channels, each of the plurality of open channels being provided with an electrode tip at a distal end, wherein each electrode tip is received within the hollow inner volume of the shaft and within a respective aperture of the applicator tip to define a respective gas flow channel defined by the electrode and the elongate shaft and by the electrode and the applicator tip, wherein each respective gas flow channel extends parallel to the longitudinal axis within the elongate shaft, and wherein each electrode tip extends radially outward with respect to the longitudinal axis to an outermost surface of the applicator tip, so that the respective gas flow channel extends radially outwards with respect to the longitudinal axis within the applicator tip.

2. An applicator as claimed in claim 1, wherein the electrode is centrally located within the inner volume.

3. An applicator as claimed in claim 1, wherein a portion of each of the plurality of open channels of the electrode within the applicator tip defines a smooth curve.

4. An applicator as claimed in claim 1, wherein a distal end of the applicator tip is provided with a counter bore.

5. An applicator as claimed in claim 4, further comprising a headed pin in the counter bore and extending through the applicator tip and the electrode in a proximal direction along the longitudinal axis.

6. An applicator as claimed in claim 5, wherein a proximal end of the headed pin is retained within the elongate shaft by engagement with a proximal end of the electrode.

7. An applicator as claimed in claim 1, wherein the applicator tip comprises a moulded ceramic.

8. An applicator as claimed in claim 1, further provided with an electrical conduit in electrical engagement with the electrode.

9. An applicator as claimed in claim 6, wherein the proximal end of the headed pin is welded to the proximal end of the electrode.

10. An applicator as claimed in claim 8, wherein the electrical conduit is welded to a proximal end of the electrode.

* * * * *